United States Patent [19]
Van Dick

[11] Patent Number: 5,480,374
[45] Date of Patent: Jan. 2, 1996

[54] METHOD AND APPARATUS FOR REDUCING PHYSIOLOGICAL STRESS

[76] Inventor: Robert C. Van Dick, 5625 Sugar Creek Ct., Norcross, Ga. 30093

[21] Appl. No.: 219,088

[22] Filed: Mar. 28, 1994

[51] Int. Cl.⁶ .................................................. A61B 17/52
[52] U.S. Cl. ............................. 600/26; 600/9; 600/14
[58] Field of Search .......................... 600/9, 10, 11, 600/12, 13, 14, 15, 26; 128/731, 722; 607/72

[56]  References Cited
U.S. PATENT DOCUMENTS

| | | | |
|---|---|---|---|
| 3,773,049 | 11/1973 | Rabichev et al. | 128/362 |
| 3,882,850 | 5/1975 | Bailin et al. | 128/2.1 |
| 3,884,218 | 5/1975 | Monroe | 128/1 |
| 3,951,134 | 4/1976 | Malech | 128/2.1 |
| 4,187,506 | 2/1980 | Dickinson | 343/100 |
| 4,388,918 | 6/1983 | Filley | 128/1 |
| 4,444,199 | 4/1984 | Shafer | 128/691 |
| 4,838,850 | 6/1989 | Rosengart | 600/14 |
| 4,846,178 | 7/1989 | Fuxue et al. | 128/419 |
| 4,998,532 | 3/1991 | Griffith | 128/419 |
| 5,066,272 | 11/1991 | Eaton et al. | 600/9 |
| 5,092,835 | 3/1992 | Schurig et al. | 600/9 |
| 5,213,338 | 5/1993 | Brotz | 273/460 |
| 5,269,746 | 12/1993 | Jacobson | 600/13 |

*Primary Examiner*—Lee S. Cohen
*Assistant Examiner*—Stephen Huang
*Attorney, Agent, or Firm*—Kennedy & Kennedy

[57] ABSTRACT

Physiological stress in a human subject is treated by generating a weak electromagnetic field about a grounded electrode by the application of pulses of between 5 and 50 microseconds each at a pulse rate of between 0.5K and 10K pulses per second to a power electrode, the power electrode and grounded electrode being coupled to high voltage pulse generation means. A subject is positioned within the weak electromagnetic field for a period of time sufficient to cause an increase in his or her alpha or theta brain wave levels.

10 Claims, 5 Drawing Sheets 5,480,374

METHOD AND APPARATUS FOR REDUCING PHYSIOLOGICAL STRESS

TECHNICAL FIELD

The present invention relates to methods and apparatuses for reducing physiological stress in humans. More particularly, the invention relates to methods of reducing physiological stress by increasing an individual's alpha and theta brain waves amplitudes without the need for conscious mental effort or the attachment of devices to the body.

BACKGROUND OF THE INVENTION

The human brain produces electrical brain waves at frequencies ranging from 0 to 64 Hertz (Hz). Within this range are delta waves from 0 to 3 Hz, theta waves from 3 to 8 Hz, alpha waves from 8 to 13 Hz, and beta waves from 13 to 64 Hz. These brain waves are usually present at any given time but in varying magnitudes depending on an individual's thought processes. Beta levels dominate during the alert awakened state. Alpha levels rise and beta levels fall in the light sleep state. Theta levels increase while alpha and beta levels decrease during the deep sleep state. Delta levels rise during a deep-deep sleep state.

It is known that an increase in physiological stress is manifested by low levels of alpha and theta brain waves. An increase in theta frequency levels produce the best physiological stress reduction results, yet they are the most difficult for individuals consciously to produce. While it has been found that an increase in theta frequency levels correspondingly increases alpha frequency levels, the reverse is not true. The more readily increased alpha brain waves do not correspondingly increase theta brain wave levels.

Current techniques used to reduce psychological stress are essentially limited to conscious mental efforts. This is sometimes achievable through pure meditation and sometimes not. Such technique is thus often unreliable. Physiological stress reduction can also be achieved by mental exercises in association with electronic bio-feedback instruments that inform individuals of their success or failure in controlling brain wave frequencies, and which assist in altering brain wave frequencies. These bio-feedback instruments typically employ sensors that are attached to the individual's skull and which are electrically coupled with analytic and display apparatuses. Since the individual is physically attached to the instrument, limitations in movement exist which can inhibit the ability of the individual to increase his or her alpha and theta brain wave frequencies and to maintain such increases for a sufficiently period of time to achieve therapeutic results.

Thus, there remains a need for a method of reducing physiological stress that does not require conscious mental effort by individuals and which does not require the attachment of devices to the persons. Accordingly, it is to the provision of such physiological stress that the present invention is primarily directed.

SUMMARY OF THE INVENTION

It has now been discovered that physiological stress reduction can also be achieved with the use of electrical means without the need for conscious effort nor the attachment of devices to persons. By merely exposing a person or persons to a weak electromagnetic field produced in a certain manner, the person's alpha and theta brain wave levels may be increased and thereby reduce physiological stress.

The weak electromagnetic field is produced about a grounded electrode that is coupled with a high voltage pulse generator. The generator transmits pulses of between 5 and 50 microseconds each, at a pulse repetition rate of between 0.5K and 10K pulses per second, to a power electrode, the power electrode and grounded electrode being coupled to a high voltage pulse generator. The subject is positioned within the weak electromagnetic field for a period of time sufficient to cause an increase in alpha and/or theta brain wave levels of the subject.

The method may be practiced with a therapeutic unit that has a treatment space of a size sufficient to accommodate one or more human subjects positioned within the weak electromagnetic field about the grounded electrode. The weak electromagnetic field itself may be specifically prescribed by monitoring brain wave levels of the subject while varying an electrical parameter of the pulse trains generated by the high voltage pulse generator and identifying that parameter which produces a desirable increase in alpha and/or theta brain wave levels for the individual.

BRIEF DESCRIPTION OF THE DRAWING

FIG. 3A represents brain wave patterns of a Subject A before utilizing the method of the present invention while

FIG. 4A represents the brain wave patterns of a Subject B before utilizing the method of the present invention while

DETAILED DESCRIPTION OF THE DRAWINGS

Figure 1:
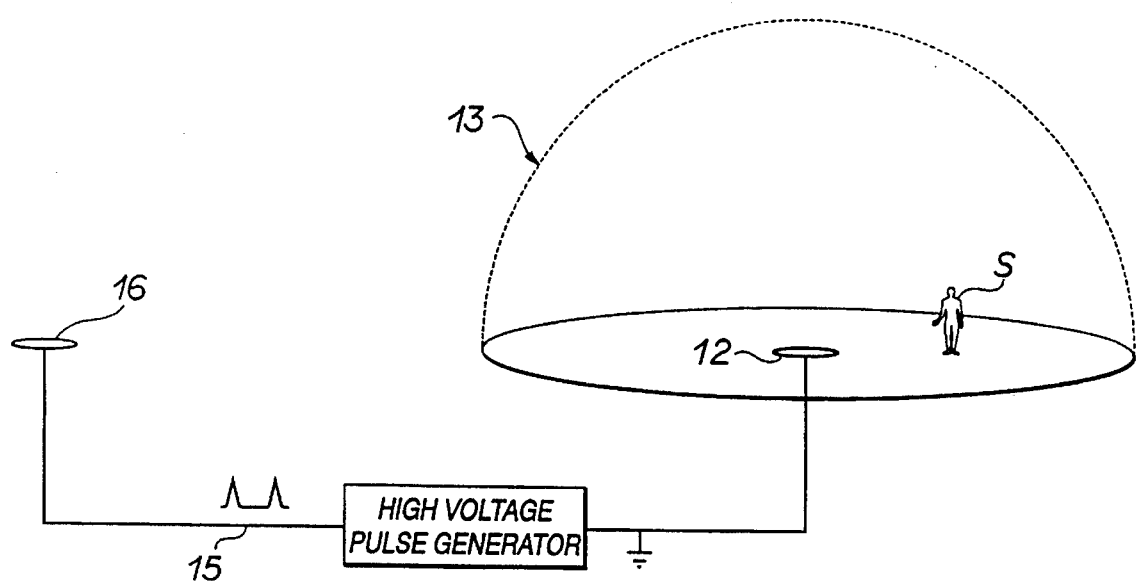
FIG. 1 is a schematic diagram of a therapeutic unit that embodies principles of the present invention.

With reference next to the drawing, there is schematically shown in FIG. 1 a therapeutic unit for the treatment of physiological stress in a human subject. The unit has means for generating a weak electromagnetic field about a grounded electrode 12 of generally semi-spherical spatial shape as indicated at 13, there of course being no sharply defined boundary of such. A human subject S is shown positioned within this weak electromagnetic field for treatment which may, for example, be in a room of a building.

The weak electromagnetic field is generated by the use of a high voltage pulse generator that is connected via a well insulated conductor to both the grounded electrode 12 and to earth ground. The generator is also connected via another insulated conductor 15 to a power electrode 16 that is located outside of the weak electromagnetic field.

Figure 2:
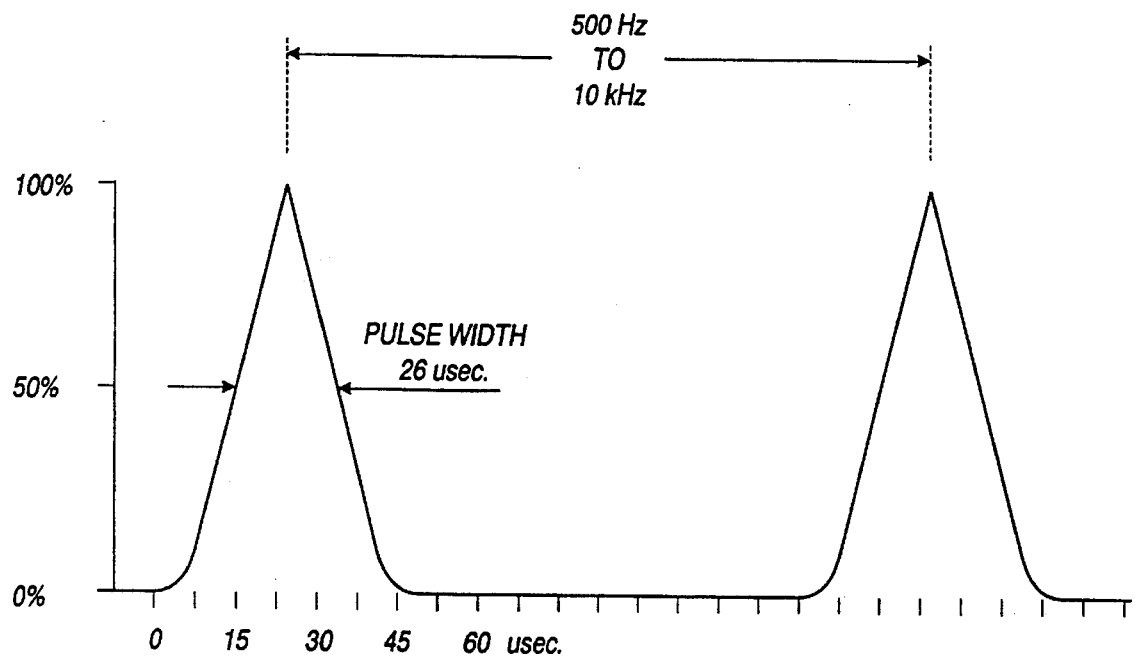
FIG. 2 is a graphic representation of a pulse train generated for use in practicing the method of the present invention.

The high voltage pulse generator is capable of generated pulses of between 0.5 KV to 30 KV of variable pulse widths and pulse repetition rates. It has been found that pulse widths of between 5 and 50 microseconds as measured at 50% of peak voltage and of a pulse repetition rate of between 500 Hz and 10K Hz, peak to peak, as shown in FIG. 2, produces a weak electromagnetic field that is of substantial therapeutic value here. Moreover, it has been determined that different pulse repetition frequencies or rates within this overall range provide better benefits for different individuals than others. Thus by observing alpha and theta levels in an individual while varying the pulse repetition rate, an optimum or at least a good rate can be determined and prescribed for treatment of that particular individual.

Figure 3A:
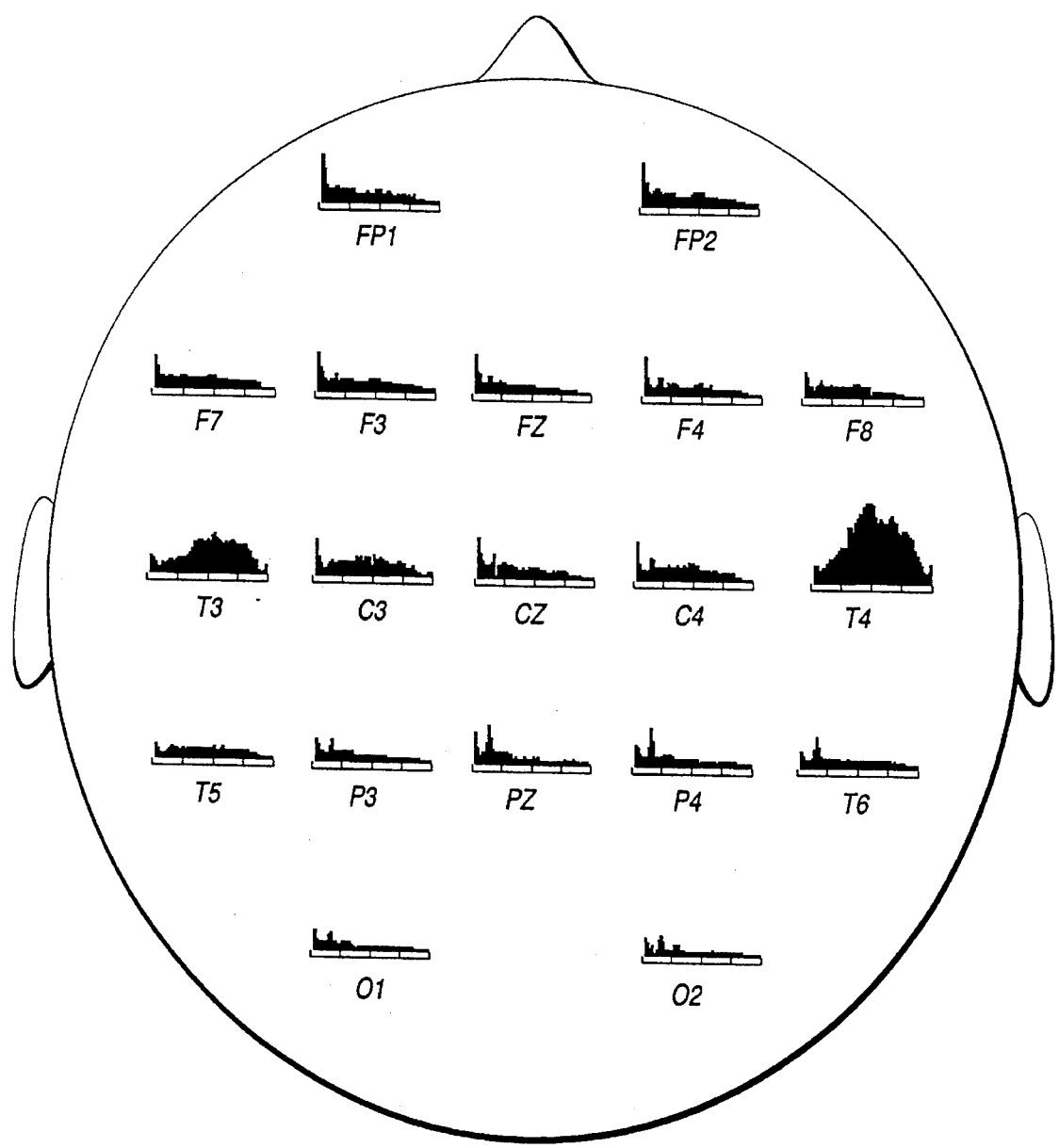
Figure 3B:
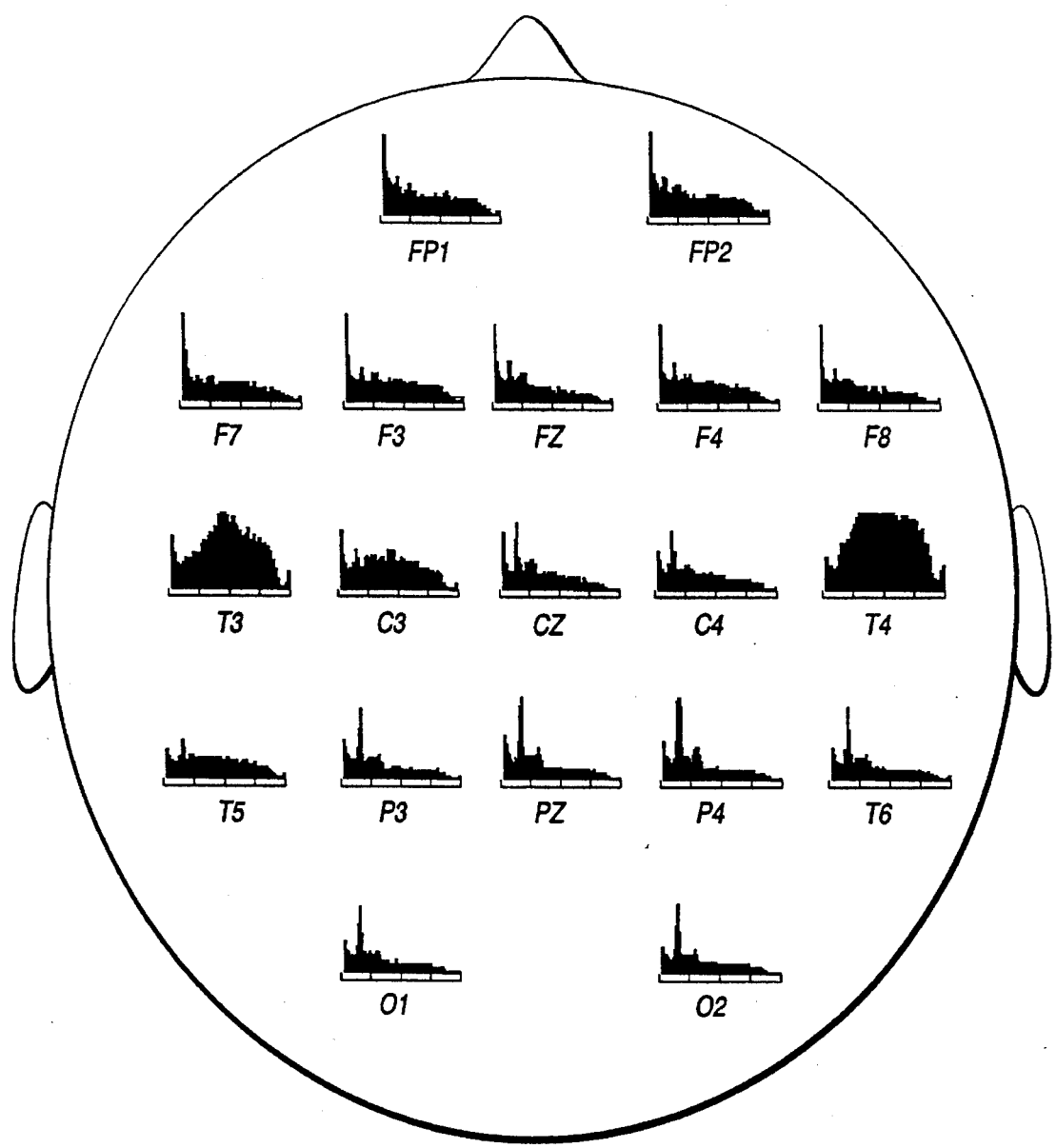
FIG. 3B represents the brain wave patterns of subject A after utilizing the method of the present invention.
Figure 4A:
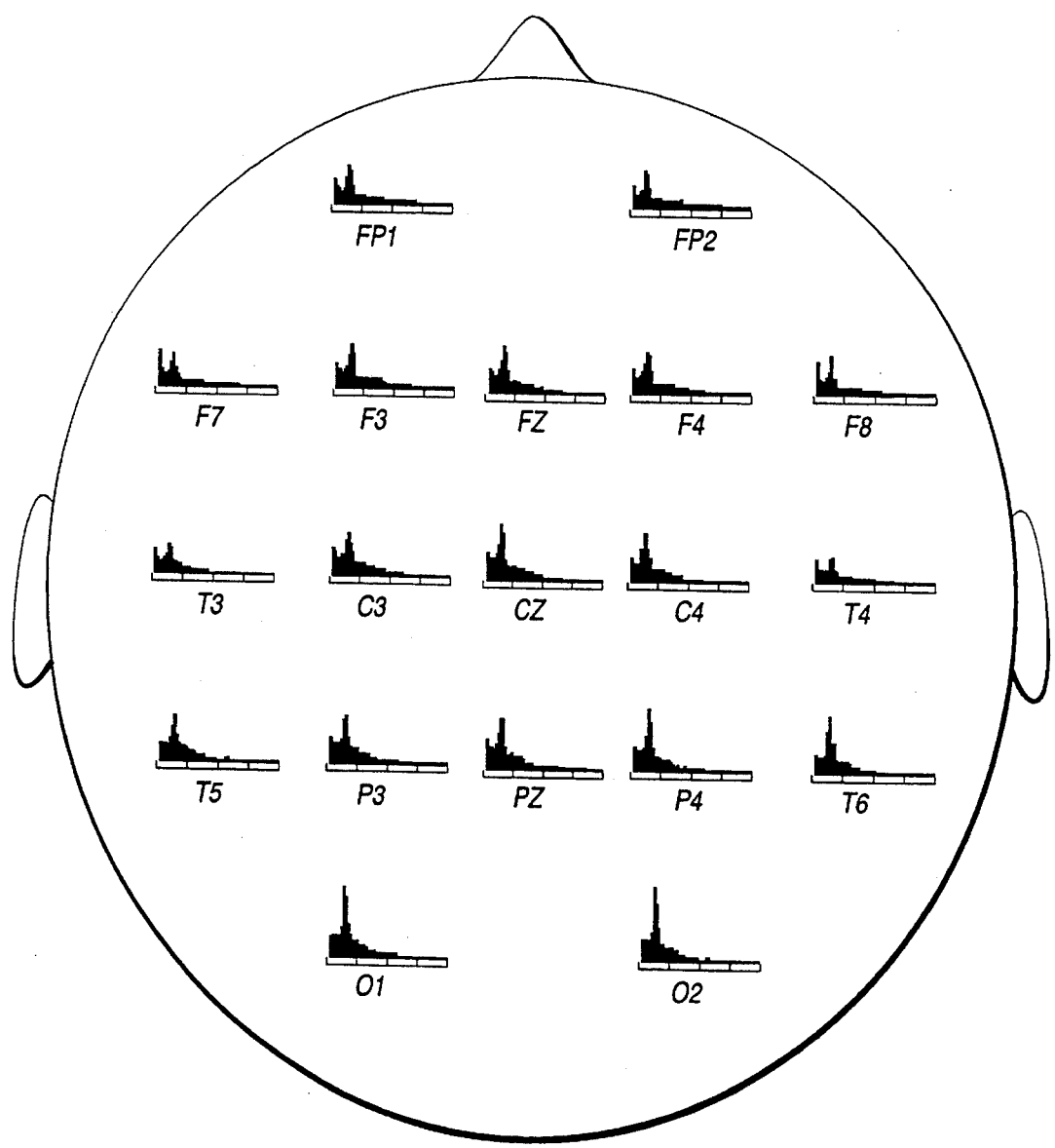
Figure 4B:
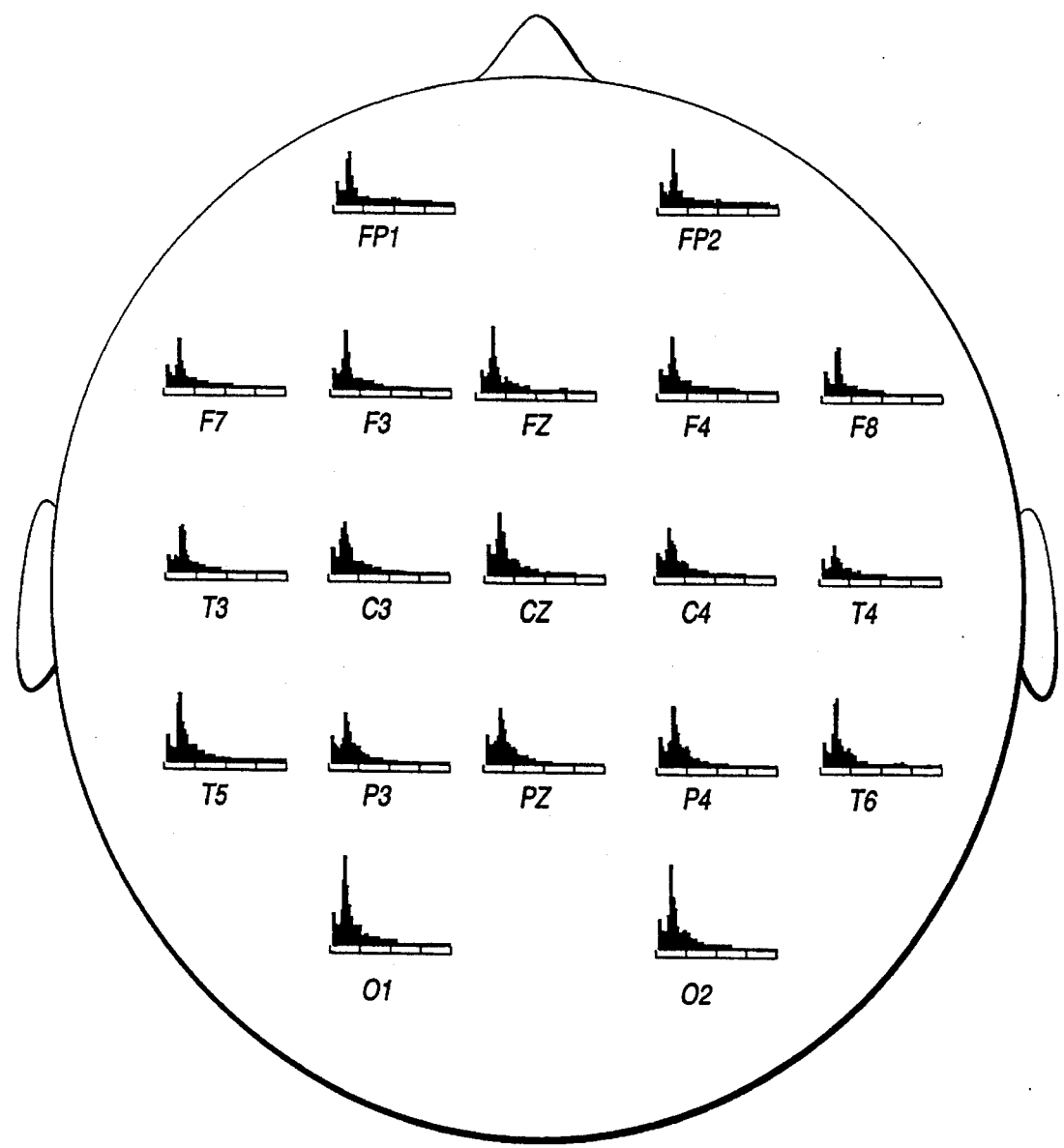
FIG. 4B represents the brain wave patterns of the Subject B after utilizing the method of the present invention.

To determine an at least good or optimum pulse repetition rate for a human subject, electroencephalograms, or EEGs, are taken prior to regular treatments with a specially designed skull cap having electrodes that sense electrical brain waves. This apparatus is conventional and may be purchased from Lexicor, Inc. of Boulder, Colorado or from E. C. I. Electro-Cap International, Inc. of Eaton, Ohio. Before and After treatment electroencephalograms for a first subject are respectively shown in FIGS. 3A and 3B while before and after treatment EEGs for a second subject are respectively shown in FIGS. 4A and 4B. The weak electromagnetic field for the treatment of the first subject was created by pulsing the power electrode with pulses of 26 microseconds each of 1500 volts peak with a pulse rise time of 15 usec from the 10% point to the 90% point of the peak voltage. The pulse repetition rate of the first subject was 2,210, 5,505 and 7,708 pulses per second. A pulse repetition rate of 7,708 was found to achieve the best results. The same parameters were applied to the second subject except that a pulse repetition rate of 7,690 pulses per second was found to be the best.

The subjects were at rest seated in a chair in a room under approximately standard temperature and pressure conditions and illuminated at low levels. The treatment sessions lasted 20 minutes. The benefit derived from the treatment was found to last at least a week.

In FIGS. 3A, 3B, 4A and 4B the designation FPI, FPZ, F7 and so forth represent locations along the skull used in practicing the International 10–20 method of generating EEGs. For example, here F means frontal, T means temporal, O is occipital, P is parietal, C is central and FP is frontal pole and so forth. The horizontal scale below each designation is from 0 to 64 Hz, left to right. Thus this scale is large enough to include both alpha and theta frequency wavebands. The irregular black lines or merged black line areas represent sensed levels or amplitudes of brain waves. High spikes in the alpha and theta frequency bands are desired as they cause or are at least associated with physiological stress reduction.

From comparisons of the observed before-treatment and after-treatment alpha and theta wave levels for these two subjects, it can be seen that both achieved an increase in their alpha and theta wave levels when they were treated in accordance with the present method. (Both appear in the first, left-side quarter of the scales.) Each also readily confirmed their feelings of stress reduction. Though such expressions were of course subjective, the detected brain wave patterns readily provided objective verification of such.

The treatment has been proven to be very effective, and repeatable with reliable results. Though a device is attached to a subject for prescribing the best pulse repetition rate for that person, for treatment itself this is not done. During treatment the individual has freedom of dress and posture and may even engage in light mental activities such as reading, eating, listening to music, etc. Treatment sessions need normally last no more than 20 minutes nor more frequently than weekly.

It thus is seen that a method of prescribing and treating, and apparatus for performing such, is now provided for treating physiological stress that alleviates problems associated with prior methods and apparatuses. Though the invention has been described in its preferred form, it should be understood that many modifications, additions and deletions may be made thereto without departure from the spirit and scope of the invention as set forth in the following claims.

I claim:
1. A method of treating physiological stress in a human subject which comprises the steps of:
   (a) generating a weak electromagnetic field about a grounded electrode by the application of pulses of between 5 and 50 microseconds each at a pulse repetition rate of between 0.5K and 10K pulses per second to a power electrode, the power electrode and grounded electrode being coupled to high voltage pulse generation means for generating high voltage pulses; and
   (b) positioning the subject within the weak electromagnetic field for a period of time sufficient to cause an increase in alpha or theta brain wave levels of the subject.

2. The treatment method of claim 1 wherein the pulses are applied at a voltage in excess of 0.5K volts.

3. The treatment method of claim 2 wherein the pulses are applied at a voltage less than 30K volts.

4. The treatment method of claim 1 wherein the power electrode generates a power electromagnetic field and wherein the pulses are applied with the grounded electrode spaced sufficiently from the power electrode so that the weak electromagnetic field is outside of the power electromagnetic field about the power electrode.

5. The treatment method of claim 1 wherein the weak electromagnetic field is generated with the grounded electrode coupled with earth ground.

6. A method of prescribing a treatment protocol for a reduction in physiological stress of a human subject which comprises the steps of:
   (a) generating a weak electromagnetic field about a grounded electrode coupled with a high voltage pulse generator, the generator also being coupled with a power electrode,
   (b) positioning the subject within the weak electromagnetic field,
   (c) monitoring brain wave levels of the subject while varying an electrical parameter of pulse trains generated by the generator and transmitted to the power electrode, and
   (d) prescribing an electrical parameter that achieves a desirable increase in alpha or theta brain wave activity for the subject as observed from the monitoring.

7. The method of claim 6 wherein step (c) the brain wave activity of the subject is monitored electroencephalographically.

8. The method of claim 6 wherein step (a) pulse trains having a pulse repetition frequency are generated and wherein step (c) the pulse repetition frequency parameter is varied.

9. A therapeutic unit for the treatment of physiological stress of a human subject and which comprises:
   (a) high voltage pulse generation means for generating pulses of between 5 and 50 microseconds each at a pulse repetition rate of between 0.5K and 10K pulses per second,
   (b) a grounded electrode coupled with said pulse generation means and located in a treatment space of a size sufficient to accommodate a human subject within a weak electromagnetic field about said grounded electrode, and
   (c) a power electrode located outside of said treatment space and coupled with said pulse generation means.

10. The therapeutic unit of claim 9 wherein said grounded electrode is coupled with earth ground.

* * * * *